US011701808B2

(12) United States Patent
Gerke et al.

(10) Patent No.: US 11,701,808 B2
(45) Date of Patent: Jul. 18, 2023

(54) CONVEYING DEVICE FOR CONVEYING A VISCOUS MATERIAL FROM A CONTAINER, AND METHOD FOR OPERATING THE CONVEYING DEVICE

(71) Applicant: Wagner International AG, Altstatten (CH)

(72) Inventors: Thomas Gerke, Haiqer (DE); Marcus Naber, Leichlingen (DE); Christian Schygulla, Meinerzhagen (DE)

(73) Assignee: Wagner International AG, Altstatten (CH)

( * ) Notice: Subject to any disclaimer, the term of this patent is extended or adjusted under 35 U.S.C. 154(b) by 1184 days.

(21) Appl. No.: 16/326,247

(22) PCT Filed: Sep. 20, 2017

(86) PCT No.: PCT/EP2017/025262
§ 371 (c)(1),
(2) Date: Feb. 18, 2019

(87) PCT Pub. No.: WO2018/054548
PCT Pub. Date: Mar. 29, 2018

(65) Prior Publication Data
US 2019/0184615 A1 Jun. 20, 2019

(30) Foreign Application Priority Data
Sep. 20, 2016 (EP) ..................... 16189665

(51) Int. Cl.
*B29B 7/76* (2006.01)
*B29C 31/06* (2006.01)
(Continued)

(52) U.S. Cl.
CPC ............ *B29C 45/1808* (2013.01); *B29B 7/74* (2013.01); *B29B 7/7626* (2013.01);
(Continued)

(58) Field of Classification Search
CPC .................. B67D 7/645; B29C 31/063; B29C 2945/76147; B29C 2945/76331;
(Continued)

(56) References Cited

U.S. PATENT DOCUMENTS

2014/0326322 A1 11/2014 Schutze

FOREIGN PATENT DOCUMENTS

DE 10 2004 038801 A1 2/2006
DE 20 2011 108222 U1 2/2012
(Continued)

OTHER PUBLICATIONS

Translation of DE 10 2004 038 801 ("Meier") (Year: 2006).*
(Continued)

*Primary Examiner* — Xiao S Zhao
*Assistant Examiner* — John J DeRusso
(74) *Attorney, Agent, or Firm* — Renner, Otto, Boisselle & Sklar, LLP

(57) ABSTRACT

A conveying device for conveying a viscous material from a container includes a follower plate that can be inserted into the container, and a pump by means of which the viscous material can be conveyed through the follower plate. Moreover, a measuring chamber for accommodation of a measuring sample of the viscous material is provided. The measuring chamber includes a closable material inlet opening for this purpose. A closable disposal line leads away from the measuring chamber. Moreover, a closable material return line extends from the measuring chamber via the follower plate into the container. The conveying device also includes a controller that is designed and can be operated appropriately such that it determines the compressibility of each of multiple measuring samples. The controller opens the disposal line or the material return line to the measuring
(Continued)

sample present in the measuring chamber as a function of the compressibility thus determined.

14 Claims, 10 Drawing Sheets

(51) Int. Cl.
| | |
|---|---|
| *F04B 15/02* | (2006.01) |
| *B67D 7/02* | (2010.01) |
| *G01N 1/20* | (2006.01) |
| *B67D 7/64* | (2010.01) |
| *F04B 49/08* | (2006.01) |
| *B29K 105/00* | (2006.01) |
| *G01F 11/02* | (2006.01) |
| *G01N 1/14* | (2006.01) |
| *F04B 23/02* | (2006.01) |
| *B29C 45/18* | (2006.01) |
| *B29B 7/74* | (2006.01) |
| *B29C 45/76* | (2006.01) |
| *B29K 83/00* | (2006.01) |
| *G01N 33/44* | (2006.01) |
| *B05B 12/08* | (2006.01) |
| *B05B 9/047* | (2006.01) |
| *B05B 9/04* | (2006.01) |
| *B05C 11/10* | (2006.01) |

(52) U.S. Cl.
CPC ............ *B29C 31/063* (2013.01); *B29C 45/76* (2013.01); *B67D 7/0227* (2013.01); *B67D 7/645* (2013.01); *F04B 15/02* (2013.01); *F04B 49/08* (2013.01); *G01N 1/20* (2013.01); *B05B 9/047* (2013.01); *B05B 9/0409* (2013.01); *B05B 12/08* (2013.01); *B05C 11/1002* (2013.01); *B05C 11/1007* (2013.01); *B29C 2945/7609* (2013.01); *B29C 2945/76103* (2013.01); *B29C 2945/76107* (2013.01); *B29C 2945/76127* (2013.01); *B29C 2945/76143* (2013.01); *B29C 2945/76147* (2013.01); *B29C 2945/76331* (2013.01); *B29C 2945/76354* (2013.01); *B29C 2945/76367* (2013.01); *B29C 2945/76648* (2013.01); *B29C 2945/76829* (2013.01); *B29C 2945/76832* (2013.01); *B29C 2945/76846* (2013.01); *B29C 2945/76876* (2013.01); *B29C 2945/76943* (2013.01); *B29K 2083/005* (2013.01); *B29K 2105/0097* (2013.01); *F04B 23/023* (2013.01); *F04B 2205/18* (2013.01); *G01F 11/021* (2013.01); *G01N 33/442* (2013.01); *G01N 33/445* (2013.01); *G01N 2001/1454* (2013.01)

(58) Field of Classification Search
CPC ............ B29K 2083/005; B29B 7/7626; F04B 2205/503; G01F 11/021; G01N 2001/205; G01N 2001/2057; G01N 2001/2064; G01N 1/2035; G01N 1/20
See application file for complete search history.

(56) References Cited

FOREIGN PATENT DOCUMENTS

| | | |
|---|---|---|
| WO | 2009/140776 A2 | 11/2009 |
| WO | 2014/056011 A2 | 4/2014 |

OTHER PUBLICATIONS

International Search Report for corresponding App. No. PCT/EP2017/025262, dated Nov. 7, 2017.
Written Opinion for corresponding App. No. PCT/EP2017/025262, dated Nov. 7, 2017.

\* cited by examiner

CONVEYING DEVICE FOR CONVEYING A VISCOUS MATERIAL FROM A CONTAINER, AND METHOD FOR OPERATING THE CONVEYING DEVICE

TECHNICAL FIELD

The invention relates to a conveying device for conveying viscous materials from a container, and to a method for operating the conveying device.

The conveying device can be used to reliably convey various medium to high viscosity materials, such as sealants, adhesives or silicone rubber, from containers, for example buckets or barrels, to various processing systems. The conveying device is also referred to as a feed system for transporting viscous materials.

Injection moulding machines can be used for the production of injection moulded parts from a viscous one-component or multi-component material, for example liquid silicone, also called Liquid Silicone Rubber (LSR). The viscous material is usually supplied in 20 L to 200 L containers by the supplier of the material. A conveying device is used to convey the material from the container and to feed it to the injection moulding machine. If multi-component materials are used, an additional mixing device may be provided by means of which the individual components can be mixed before feeding them to the injection moulding machine.

PRIOR ART

A conveying and mixing device of this type for the mixing of two liquids is known from printed specification, WO 2014/056011 A2. The conveying and mixing device comprises a pump that is connected to a follower plate. In conveying operation, the follower plate rests on the liquid in the container and is sealed with respect to the container. The pump conveys the liquid through the follower plate from the container. When containers are exchanged, air may ingress between the surface of the liquid and the follower plate. In order to remove the air from this location, a pressure transducer mounted on the pump outlet is used to measure the conveying pressure generated by the pump. Subsequently, the measured conveying pressure is compared to a target value and a ventilation valve integrated into the follower plate is opened so often and for so long that the conveying pressure is identical to the target value, after which the ventilation valve stays closed. It is presumed in this context that an air-free liquid has its specific conveying pressure applied to it, which changes when air is being enclosed. However, this solution is associated with the following disadvantage. If a measurement detects that the measured conveying pressure corresponds to the target value, then it is presumed that only air-free liquid is being conveyed from then on. This is not necessarily the case. It is possible that there is still air present in the liquid, whereas the measuring sample used was free of air by coincidence. In this case, the solution described above conveys air-containing liquid later on without this being detected. If one wishes to circumvent this disadvantage, a number of measuring samples would need to be taken and the liquid would have to be conveyed to the injection moulding machine only once multiple measurements on different measuring samples confirmed that the liquid no longer contains air. This procedure would lead to high losses of material though, because not only the air-containing measuring samples, but also the air-free measuring samples would have to be discarded until it was certain that no air-containing measuring sample follows. Accordingly, the solution described above is either associated with a disadvantage in that it cannot be truly made certain that air-free liquid is being conveyed or in that relatively much liquid—including air-free and therefore usable liquid—needs to be discarded before it is has been as-certained that the liquid is free of air.

DESCRIPTION OF THE INVENTION

It is one object of the invention to devise a conveying device for the conveying of a viscous material from a container and an operating procedure, in which it is as-certained that only bubble-free material is being conveyed and in which the fraction of material to be discarded is minimised.

The object is met by a conveying device for conveying a viscous material from a container having the features specified in patent claim 1.

The conveying device according to the invention for conveying a viscous material from a container comprises a follower plate that can be inserted into the container, and a pump by means of which the viscous material can be conveyed through the follower plate. Moreover, a measuring chamber for accommodation of a measuring sample of the viscous material is provided. The measuring chamber 85 comprises a closable material inlet opening 85.1 for this purpose. A closable disposal line leads away from the measuring chamber. Furthermore a closable material return line is provided, which leads from the measurement chamber via the follower plate into the container. The conveying device also comprises a controller that is designed and can be operated appropriately such that the controller determines the compressibility of each of a plurality of measurement samples. The controller opens the disposal line or the material return line to the measuring sample present in the measuring chamber as a function of the compressibility thus determined.

Moreover, the invention proposes a method for operating the conveying device described above, comprising the following steps. The material and/or a measuring sample of the material is conveyed into the measuring chamber. Once the material feed line, the disposal line, and the material return line are closed, the compressibility of the material contained in the measuring chamber is determined. A controller is used, as a function of the compressibility thus determined, to dispose the material contained in the measuring chamber via the disposal line or to return said material into the container via the material return line.

The conveying device according to the invention can be used for conveying a viscous material.

Advantageous developments of the invention result from the features specified in the dependent patent claims.

One embodiment of the conveying device according to the invention for conveying a viscous material provides an actuator by means of which a certain pressure can be set in the measuring chamber. Moreover, the invention provides a sensor for determination of the change of the volume of the measuring chamber. Applying a pressure to the measuring sample, the detected volume change can be used to determine the compressibility of the measuring sample. Since air is many times more compressible than the viscous material, the compressibility of the measuring sample can be used as an easy means for determining, at sufficient certainty, whether or not any air is present in the measuring sample.

In an alternative embodiment of the conveying device according to the invention, the pump comprises a pump actuator by means of which a certain volume can be set in the measuring chamber. A sensor for determining the pressure in the measuring chamber is provided as well. This also allows the compressibility of the measuring sample to be determined. Moreover, it is an option for determining whether or not there is any air in the measuring sample.

In another embodiment of the conveying device according to the invention, the actuator is a piston or a membrane. The piston can be, for example, the piston of the pump or a separate piston.

An additional embodiment of the conveying device according to the invention provides a sensor for detection of the actuator position. Sensors for detection of the actuator position are inexpensive and yield reliable and in-formative measuring signals. A position sensor can be used to determine the actuator position at any time and rapidly. In addition, a position sensor is versatile in use. It can be used without further ado to detect the stroke of a piston or of a membrane or the angle position or angle change of a rotating shaft and transmit this in-formation to the controller, for example as an analogue or digital signal. Advantageously, the position sensor can be arranged outside of the measuring chamber. As a result, the compression of the measuring sample is not affected by the sensor, which is not necessarily the case during a pressure measurement in the measuring chamber by means of a pressure sensor. Arranged on or in the measuring chamber, the pressure sensor undergoes a deformation and thus affects the volume of the measuring chamber.

In a development of the conveying device according to the invention, the controller utilises the signal of the sensor in order to determine the compressibility of the measuring probe contained in the measuring chamber.

In another development of the conveying device according to the invention, the travel sensor is provided in the form of a magnetostrictive sensor.

In an additional development of the conveying device according to the invention, the pump can supply material to the measuring chamber via the material feed line.

Alternatively, the measuring chamber can be part of the pump in the conveying device according to the invention. This allows the number of components that are required to be reduced.

In the conveying device according to the invention, the pump can be provided in the form of a piston pump, gear type pump, spindle pump or eccentric screw pump.

Moreover, the follower plate can comprise a ventilation valve in the conveying device according to the invention. This can be used ahead of time to discharge part of the air that is contained in the space between the material to be conveyed, the follower plate, and the container wall.

Moreover, the conveying device according to the invention can provide the follower plate to be slanted in design in the region, in which its pressure-active area is situated. This allows the pressure acting on the material to be conveyed to be partially increased, and it can be made sure that the material tends to flow in a certain direction, for example towards the conveying opening.

In an embodiment of the conveying device according to the invention, the material feed line comprises a valve. Said valve is preferably provided appropriately such that it can be triggered by the controller.

If the measuring chamber is part of the pump, the valve in the material feed line can be a non-return valve that opens automatically, when the measuring chamber is being filled, and closes automatically, when material is being conveyed from the measuring chamber and/or in measuring mode.

The material feed line can be integrated into the piston of the pump.

In another embodiment of the conveying device according to the invention, the material return line comprises a valve. Said valve is preferably provided appropriately such that it can be triggered by the controller.

In an additional embodiment of the conveying device according to the invention, the disposal line comprises a valve, which preferably is provided appropriately such that it can be triggered by the controller.

Moreover, the invention proposes a conveying system that comprises a first and a second conveying device of the type described above, whereby the first conveying device and the second conveying device are connected, on the output side, to a mixing unit. This can be used to mix different materials, for example a component A and a component B, with each other and to convey them to a processing station, for example an injection moulding machine.

SHORT DESCRIPTION OF THE DRAWINGS

In the following, the invention is illustrated in more detail by multiple exemplary embodiments on the basis of ten figures.

FIGS. 7*a* to *d* show various operating states of the conveying device based on four block diagrams.

FIGS. 8*a* to *d* show various operating states of a further possible embodiment of the conveying device based on four block diagrams.

FIGS. 9*a* to *d* show various operating states of another possible embodiment of the conveying device based on four block diagrams.

Figure 10A:
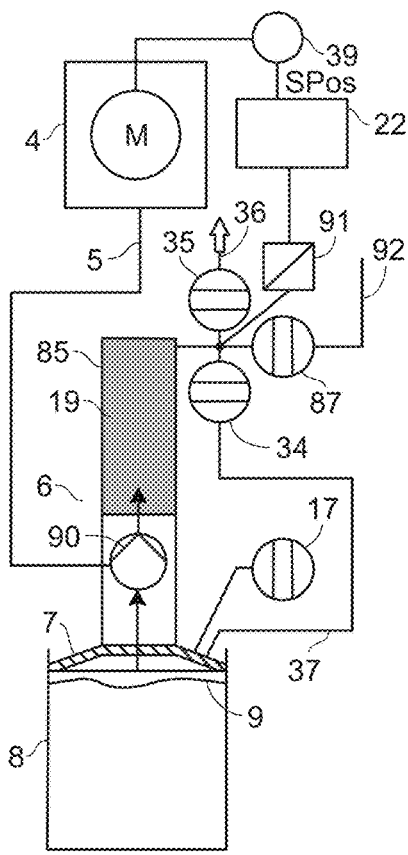
Figure 10B:
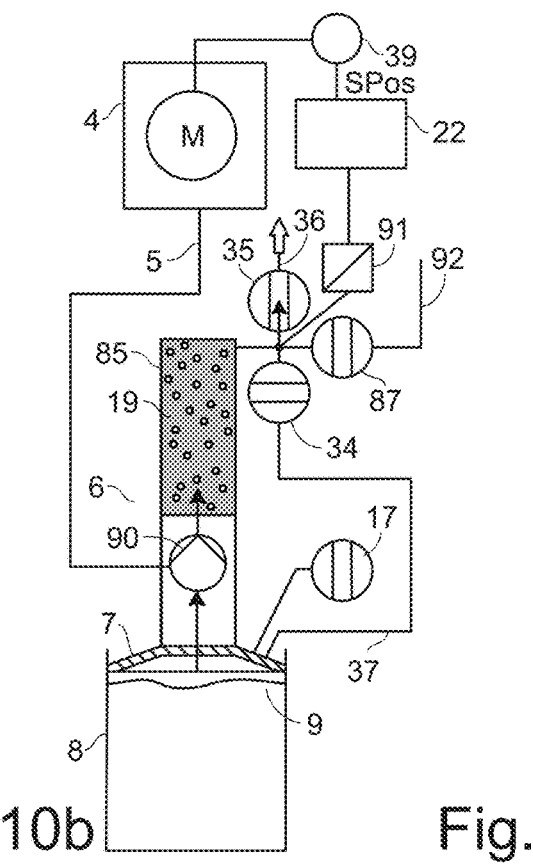
Figure 10C:
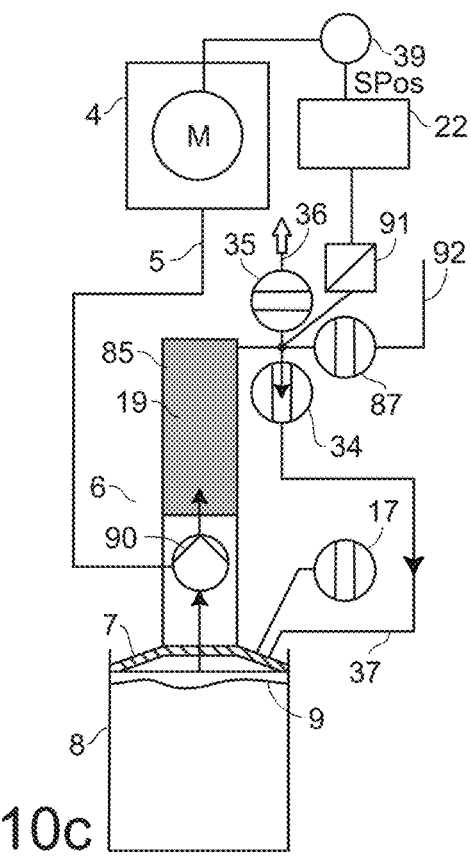

FIGS. 10*a* to *c* show various operating states of an additional possible embodiment of the conveying device based on three block diagrams.

IMPLEMENTATION OPTIONS OF THE INVENTION

The structure of a first possible embodiment of a conveying system 1 for conveying viscous material is illustrated in more detail in the following. The conveying system 1 shown in FIGS. 1, 2, and 3, comprises a first conveying device 2, by means of which, for example, a component A can be conveyed, and a second conveying device 102, by means of which, for example, a component B can be conveyed. As a matter of principle, the two conveying devices 2 and 102 can be identical in design. But this does not have to be the case. The two conveying devices 2 and 102 will be presumed to be identical in design. The reference number of the component of the second conveying device number 102 will be higher by 100 than the reference number of the component of the first conveying device 2 that is identical in design.

Figure 6:
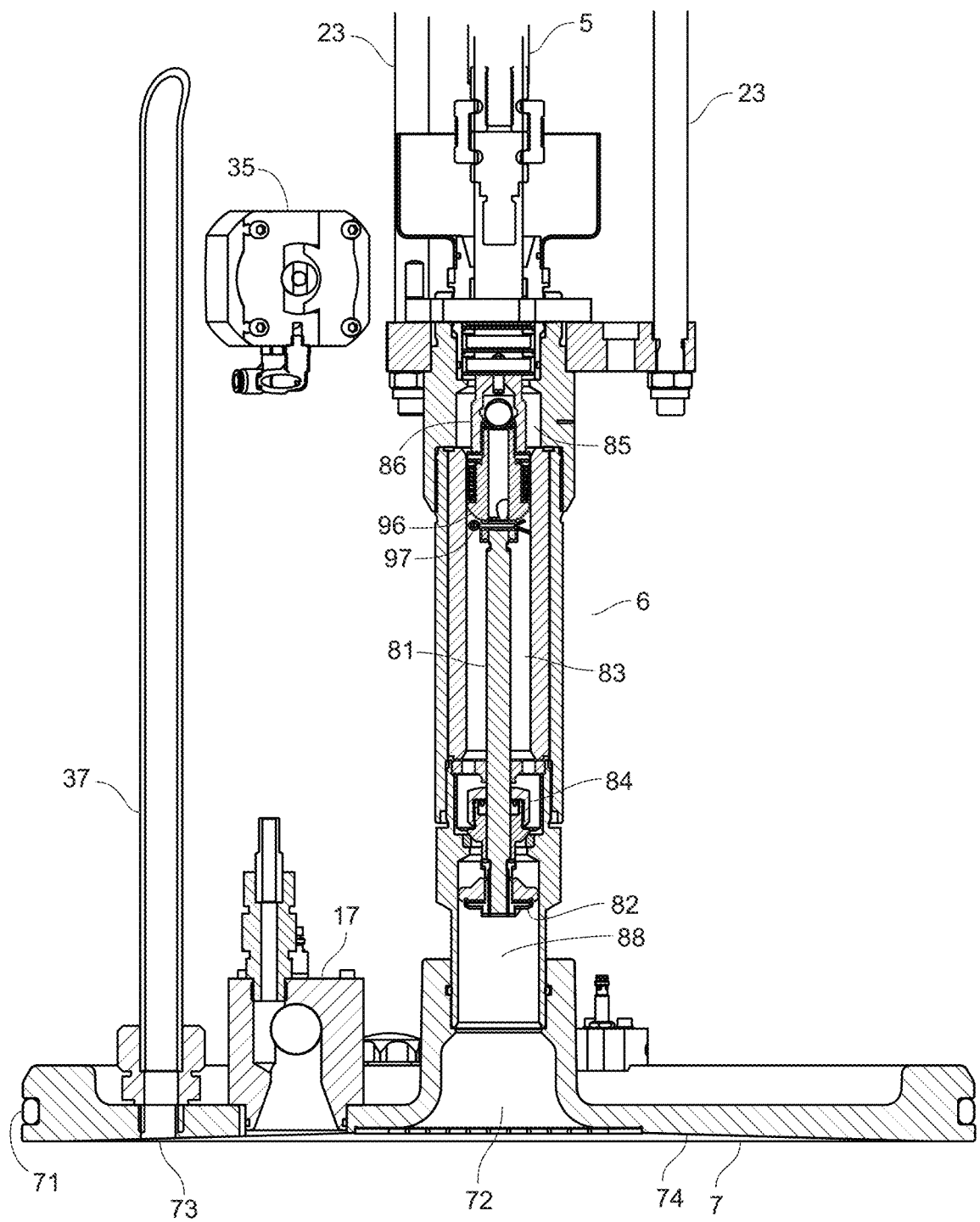
FIG. 6 shows a longitudinal section of a possible embodiment of the pump of the conveying device.

The conveying device 2 comprises a pump 6 that is driven by means of a drive 4 and a drive rod 5. If the pump 6 is provided in the form of a scoop piston pump, as shown in FIG. 6, the drive 4 is designed appropriately such that it causes the drive rod 5 to perform a stroke motion that is being transferred to the scoop piston pump. The pump 6 can just as well be a piston pump without a scoop piston rather than the scoop piston pump. The scoop piston is advantageous in the case of highly viscous materials in that the viscous material is scooped directly to the pump inlet. This allows the suction behaviour of the pump to be improved. If the pump 6 is provided in the form of a gear type pump, spindle pump or as an eccentric screw pump, the drive is designed appropriately such that it causes the drive rod 5 to perform a rotary motion that is being transferred to the gear type pump, spindle pump and/or eccentric screw pump.

The present exemplary embodiment presumes the pump 6 to be a scoop piston pump. FIG. 6 shows in exemplary manner the possible design of a scoop piston pump of this type based on a longitudinal section. A follower plate 7 is situated below the pump 6 and can have a container with the material to be conveyed inserted into it. The follower plate 7 is preferably configured with a ring-shaped seal 71 to allow the follower plate 7 to touch in sealing manner against the container wall. The seal 71 makes sure that no material leaks between the follower plate 7 and the container wall. The follower plate 7 comprises a pressure-active surface 74, which advantageously is designed to be at least partially slanting. This allows the pressure acting on the material to be conveyed to be partially increased, and it can be made sure that the material tends to flow towards the conveying opening 72 of the follower plate 7. The pump 6 can convey the viscous material through the conveying opening 72 out of the container. For this purpose, the scoop piston pump comprises a scoop piston 81, whereby a scoop piston plate 82 is situated at its lower end. In order to convey material from the container, the scoop piston 81 is moved downward such that the scoop piston plate 82 dips into the material and takes up material. During the upward motion of the scoop piston 81, the scoop piston plate 82 takes along the material through the conveying opening 72 into the inside of the pump. From there, the material gets through a first non-return valve 84 upwards into a lower pump chamber 83. During the subsequent downward motion of the drive 5 and of the scoop piston 81 connected to it, the material gets through a second non-return valve 86 into an upper pump chamber 85. The subsequent upward motion of the scoop piston 81 transports the material from the pump 6 into a material feed line 38. Accordingly, material is being transported into the material feed line 38 with each upward stroke of the scoop piston 81. The first non-return valve 84 can be provided as a seat valve and the second non-return valve 86 can be provided as a ball valve.

The drive 4 is attached to a motor mount 18. The latter, in turn, is attached to a yoke 10 by means of a first and a second rod 13, 15, respectively. The two rods 13 and 15 can be provided in the form of tubes and also serve as guidances for two lifting rods 14 and 16, respectively. The follower plate 7 is attached to the two lifting rods 14 and 16. The pump 6 can be attached to the motor mount 18 by means of further rods 23.

The yoke 10 is supported by two lifting cylinders 11. The lifting cylinders 11, the yoke 10, and the rods 13 to 16 form a pump lifting system, whose purpose is to be able to lift and lower the drive 4 along with the pump 6 and the follower plate 7.

Figure 4:
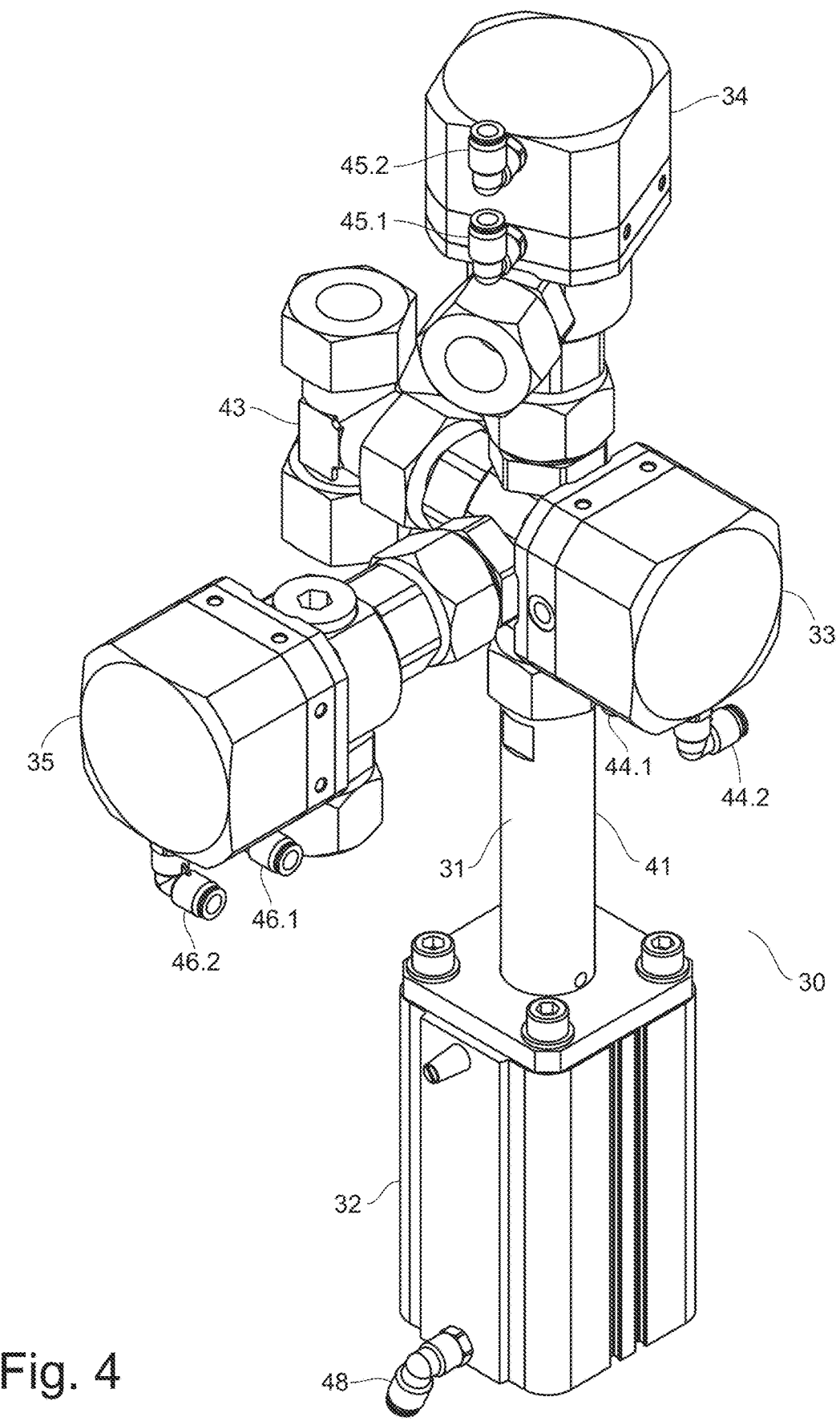
FIG. 4 shows a three-dimensional view of a possible embodiment of a mixing device, which is part of the powder conveying device.
Figure 5:
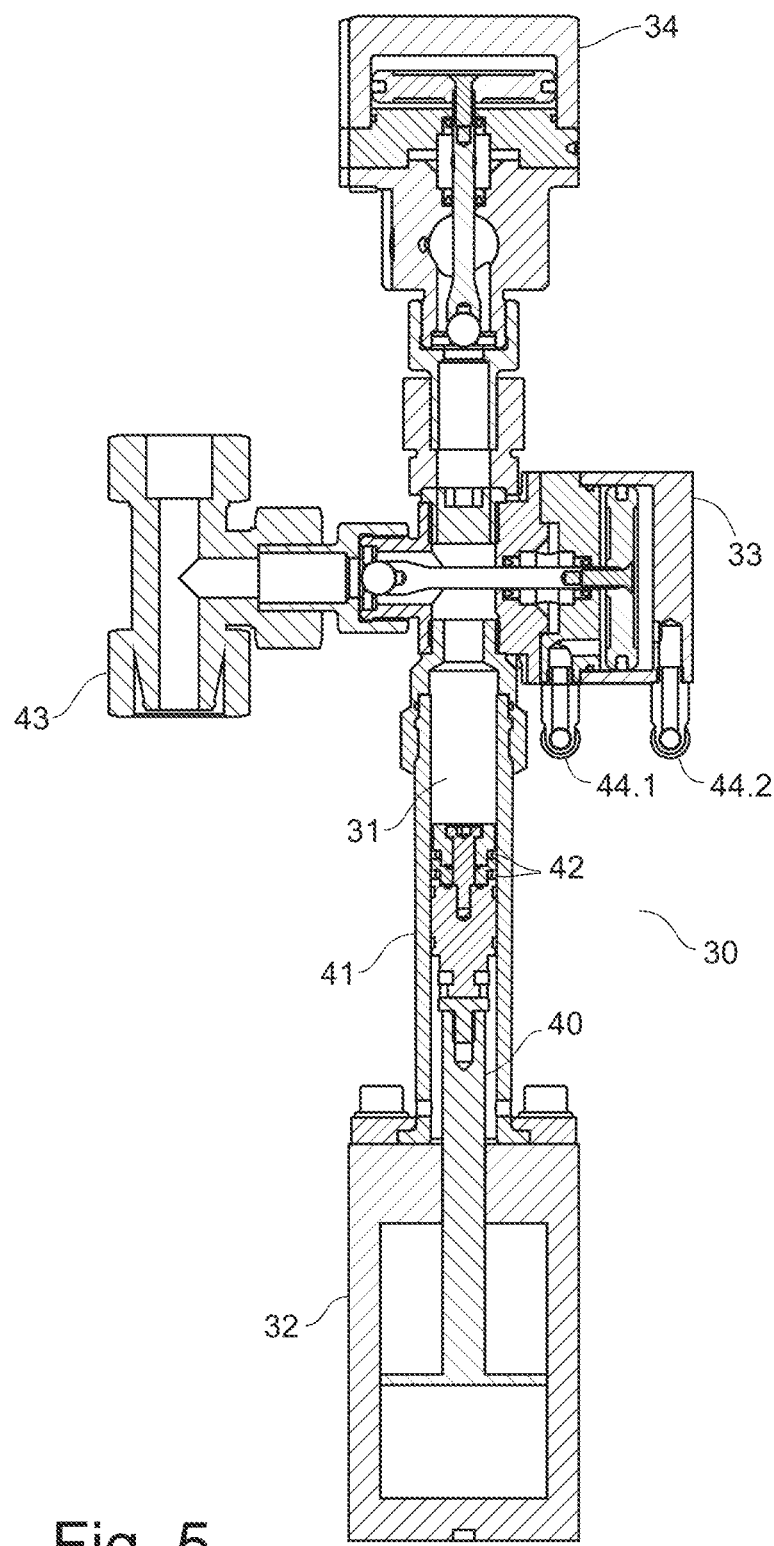
FIG. 5 shows a longitudinal section of the measuring device.

The measuring device 30 shown in FIGS. 4 and 5 is one possible embodiment and can be part of the conveying device 2. FIG. 4 shows a three-dimensional view and FIG. 5 shows a side view, sectioned, of the measuring device 30. The measuring device 30 comprises a measuring chamber 31 in a measuring chamber housing 41, whereby the volume of the measuring chamber 31 can be changed by means of a piston 40. The position of the piston 40 can be set by means of a pneumatic cylinder 32. The farther the piston 40 projects from the cylinder 32, and thus projects into the measuring chamber 31, the smaller is the volume inside the measuring chamber 31. A piston seal 42 is situated on the upper end of the piston 40 in order to seal the measuring chamber 31 in downward direction towards the cylinder 32. In order to be able to apply compressed air DL to the cylinder 32, a corresponding control port 48 is provided on the cylinder 32. The control port 48 can be used to apply compressed air DL to the piston 40 in the cylinder 32, and to move the piston. As shown in FIGS. 4 and 5, the measuring chamber housing 41 can be provided to be tube shaped. An opening is situated on the upper end of the measuring chamber housing 41, by means of which the material to be tested, i.e. the measuring sample, can get into the measuring chamber 31 and by means of which the measuring sample can also be conveyed out of the measuring chamber 31 again.

By means of an inlet valve 33, which can be provided, for example, as a needle valve, the material to be tested can be conveyed via a material feed line 38 (see FIGS. 1 to 3) and a material inlet opening 31.1 into the measuring chamber 31. The material feed line 38 shall be referred to as feed line, in short, hereinafter. It can be connected to the inlet valve 33 through a T-piece 43. When the measuring unit 30 is not in use, the conveyed material can be directed someplace else by means of the T-piece 43. The inlet valve 33 can be provided in the form of a pneumatically driven valve having two control ports 44.1 and 44.2. Applying compressed air to the control port 44.1, the piston in the valve 33 causes the material inlet of the valve to be opened such that the measuring sample gets into the measuring chamber 31. Applying compressed air to control port 44.2 instead, the piston in the inlet valve 33 causes the material inlet of the valve to be closed.

Using an outlet valve 34, which is also called a return valve, the material to be tested/measuring sample can be conveyed via a material return line 37 (see FIGS. 1 to 3) out of the measuring chamber 31 and back into the container with the material to be conveyed. The material return line 37 shall be referred to as a return line, in short, hereinafter. The outlet valve 34 can be provided in the form of a pneumatically driven valve with two control ports 45.1 and 45.2. Applying compressed air to control port 45.1, the piston in the outlet valve 34 causes the material outlet of the valve to be opened. Applying compressed air to control port 45.2 instead, the piston in the outlet valve 34 causes the material outlet of the valve to be closed such that the return line 37 is closed.

Using another outlet valve 35, the material to be tested can be conveyed via a material disposal line 36 (see FIG. 1 to 3) out of the measuring chamber 31 and, for example, into a waste container that is not shown here. The material disposal line 36 shall be referred to as disposal line, in short, hereinafter. The outlet valve 35 can be provided in the form of a pneumatically driven valve having two control ports 46.1 and 46.2. Applying compressed air to control port 46.1, the piston in the outlet valve 35 causes the material outlet of the valve to be opened. Applying compressed air to control port 46.2, the piston in the valve 35 causes the material outlet of the valve to be closed such that no material gets into the disposal line 36.

FIGS. 7a to 7d show four different operating states of the conveying device 2 based on four block diagrams. The operating states shown apply analogously to the conveying device number 102 as well, if one is present.

The conveying device 2 can be operated in conveying mode or in ventilating mode.

In conveying mode, the conveying device 2 uses the pump 4 to convey the viscous material from the container 8.

Figure 1:
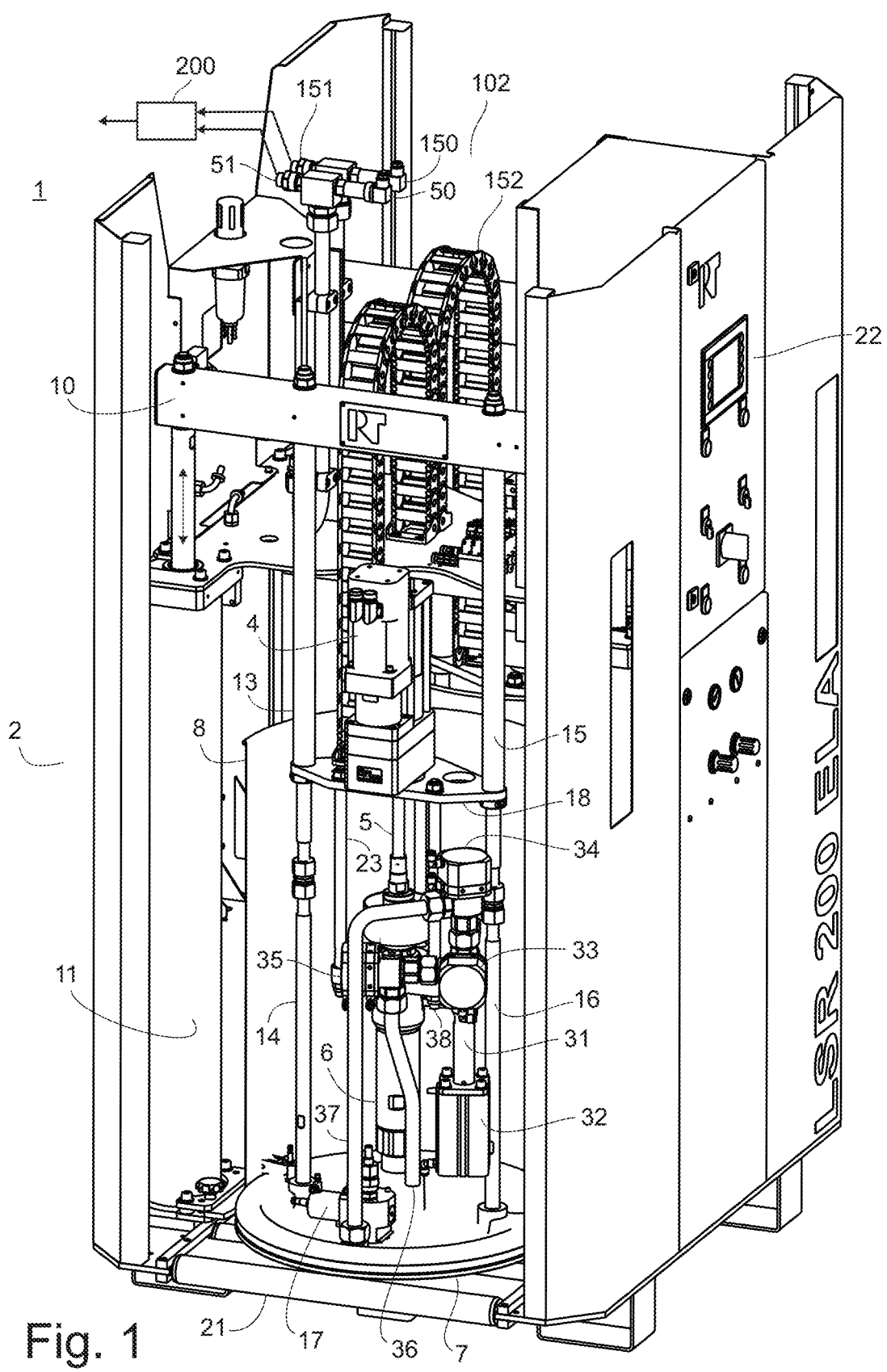
FIG. 1 shows a three-dimensional view of a conveying system with a possible embodiment of the powder conveying device according to the invention.
Figure 2:
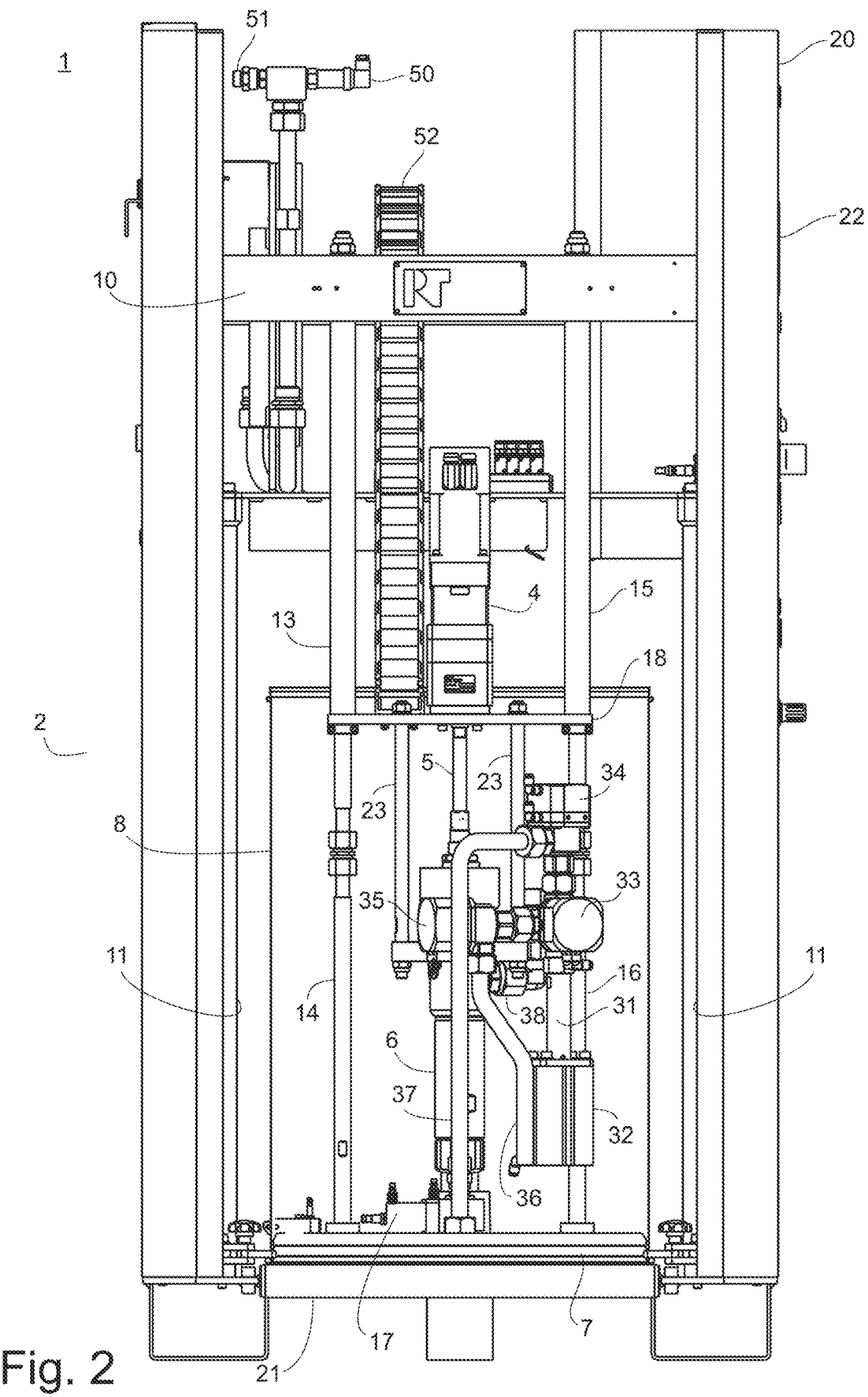
FIG. 2 shows a side view of the conveying system with the conveying device according to the invention.
Figure 3:
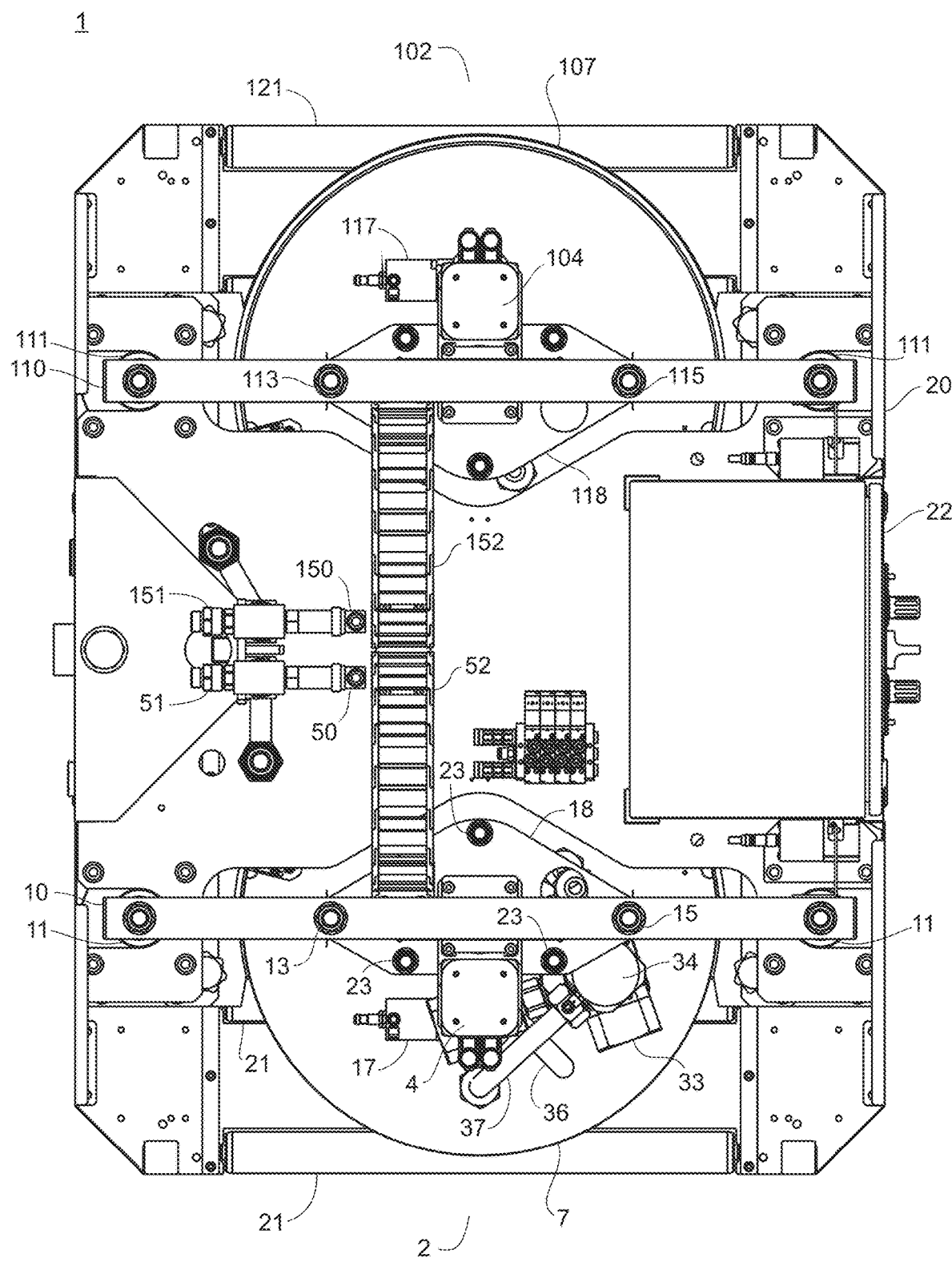
FIG. 3 shows a top view of the conveying system with the conveying device according to the invention.

In the embodiment shown in FIGS. 1 and 2, the conveying device 2 conveys component A to the outlet 51, and the conveying device 102 conveys component B to the outlet 151. From there, the two components A and B can be guided to a mixing unit 200 and/or a processing station. Pressure transducers 50 and 150 can be provided on the outlets 51 and 151, respectively.

When the container in the conveying device 2 is empty, the conveying mode is interrupted. The pump lifting system is then used to lift the pump 4 along with the follower plate 7 appropriately until the follower plate 7 is situated above the container. Then the empty container is pulled out of the conveying device 2 and a full container is pushed into the conveying device 2 and is positioned below the follower plate 7, whereby transport castors 21 ease the processes of pulling out and pushing in the container.

Subsequently, the pump lifting system is used to lower the pump drive 4 and the pump 6 along with the follower plate 7 appropriately until the follower plate 7 in the container rests on the material 9 to be conveyed. In the course of this process, air may get trapped between the surface of the material 9 to be conveyed, the container wall, and the follower plate 7.

The ventilating mode shall be described in more detail in the following.

To remove the trapped air from this location, the follower plate 7 can first be made to rest on the material 9 to be conveyed for a certain period of time during a first ventilating phase in order to give the material time to distribute. The period of time (resting time) can, for example, be adapted to the viscosity of the material. Subsequently, the ventilating valve 17 on the follower plate 7 is opened such that the air under the follower plate 7 can escape. Then the ventilating valve 17 is closed again. This procedure is advantageous, but not obligatory.

Figure 7A:
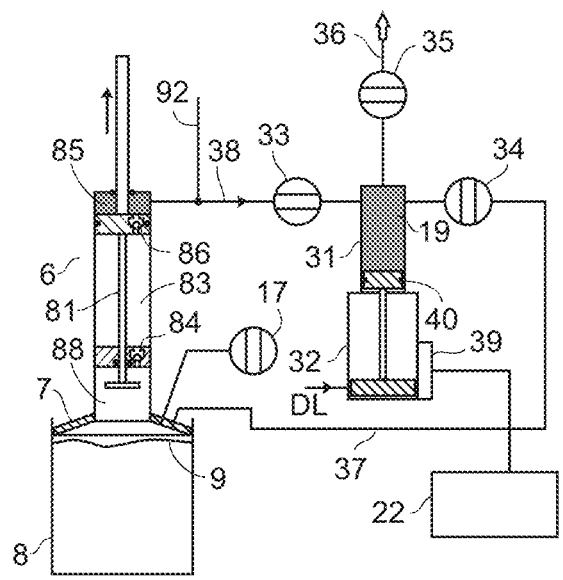

In a second ventilating phase, the remaining air is removed from the container. In this context, the controller 22 can be used to distinguish between usable (air-free) and non-usable (air-containing) material. For this purpose, the inlet valve 33 is opened, the outlet valve 34 and the discharge valve 35 are closed. It is of advantage to the ventilating mode to have the material transport line 92 be closed. The material 9 and/or the measuring sample 19 is transported out of the container 8 and into the measuring chamber 31 via the material feed line 38 (FIG. 7a). This takes place by the cylinder 32 pulling the piston 40 out of the measuring chamber 31. As a result, the volume in the measuring chamber 31 is increased and a negative pressure is generated in the measuring chamber 31 that aspirates the material into the measuring chamber 31. Alternatively or complementary, the material can also be pumped into the measuring chamber 31 by means of the pump 6.

Figure 7B:
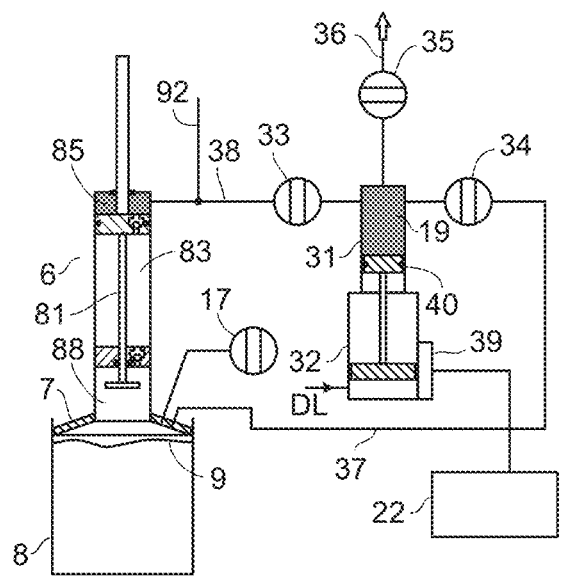

Subsequently, the material feed line 38 is closed by closing the inlet valve 33 (FIG. 7b). The two outlet valves 34 and 35 stay closed. Then, a defined pressure is applied to the cylinder 32 such that a defined pressure p is also being applied in the measuring chamber 31 by means of the piston 40. The path x travelled by the piston 40 is measured in a next step. In this context, the travelled path x is a measure of the compressibility of the material that is present in the measuring chamber 31, i.e. the measuring sample 19. If there is air in the measuring chamber, and therefore in the material, the piston 40 travels farther than when the material is free of bubbles. This is the case because the material itself is hardly compressible, whereas air is strongly compressible as compared to the material. The controller 22 compares the measured travelled path x of the piston 40 to a reference value xref.

Figure 7C:
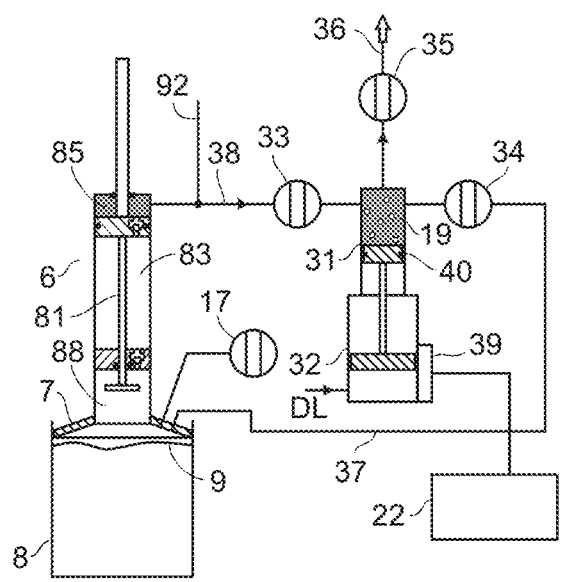
Figure 7D:
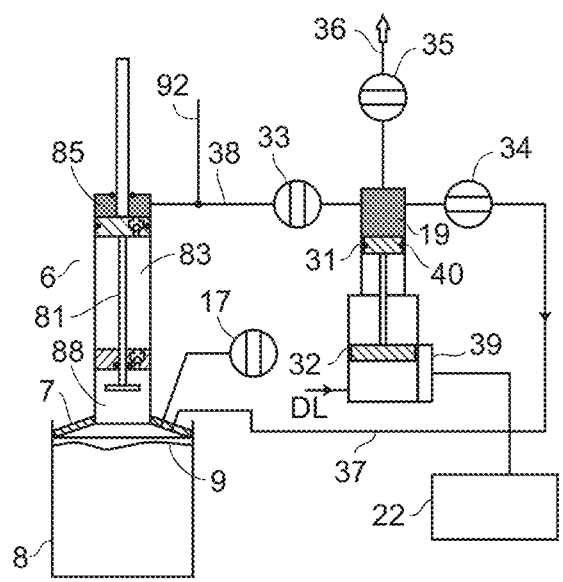

If the controller 22 detects the measured travelled path x to be larger than the reference value xref, the material is classified to be not free of bubbles (FIG. 7c). In this case, the outlet valve 35 is being opened, whereas the two other valves 33 and 34 stay closed. The measuring sample 19 (material and air) is pushed out of the measuring chamber 31 by means of the piston 40 and is disposed, for example, into a waste container via the disposal line 36.

If the controller 22 classifies the material that is present in the measuring chamber 31 to be free of bubbles and therefore usable (FIG. 7d), the outlet valve 34 is being opened, whereas the two other valves 33 and 35 stay closed. The material (measuring sample 19) is pushed out of the measuring chamber 31 by means of the piston 40 and is returned into the container 8 via the material return line 37.

In order to make sure that no residual air is still present in the container 8, the process described above can be repeated once or multiply. For this purpose, the outlet valve 34 is closed again and the inlet valve 33 is opened. The discharge valve 35 stays closed (FIG. 7a). Subsequently, another measuring sample (new material) is transported out of the container 8 and into the measuring chamber 31. The aforementioned steps can now be repeated. If the controller 22 no longer classifies material as bubble-containing after repeated performance of the afore-mentioned steps during any compression measurement, i.e. none of the measuring samples, it can be presumed that there is no longer any air contained between the follower plate 7, the surface of the material 9 to be conveyed, and the container wall. To make sure of this, for example the following can be provided. Only when the controller 22 classifies the tested material to be free of bubbles in six subsequent measurements and therefore in six subsequent measuring samples 19, the material 9 that is present in the container 8 is considered to be free of bubbles.

In order to further reduce the probability of erroneous release of the material 9 for conveyance, the following can be provided just as well. Only when the controller 22 classifies the tested material to be free of bubbles in eight subsequent measurements and therefore in eight subsequent measuring samples 19, the entire material is considered to be free of bubbles.

Accordingly, the larger the number of measuring samples 19 detected to be free of bubbles, the lower is the probability of erroneous release of the conveyance of the material 9.

If the controller 22 declared the material 9 in the container 8 to be useful after a series of tested measuring samples 19, the controller can cause the conveying device 2 to switch from ventilating mode back into conveying mode.

Alternatively, the controller 22 can be provided appropriately such that it can do the following. In a first testing cycle, a first measuring sample is drawn and ana-lysed for the presence of air in it. If the material of the measuring sample is classified to be free of bubbles, it is returned into the container 8 via the material return line 37. If the tested material is classified to be not free of bubbles, it is disposed via the material disposal line 36. Subsequently, a second measuring sample is drawn in a second testing cycle and handled in the same manner as the first measuring sample. In total, n consecutive testing cycles with n measuring samples can be conducted, whereby each of the n testing cycles pro-ceeds analogous to the first testing cycle. After a switch of barrels, for example n=8 testing cycles can be run and therefore n=8 measuring samples can be drawn; after the eighth testing cycle, the controller 22 switches from ventilating mode to conveying mode. The number n of consecutive testing cycles can just as well be, for example, n=5, 6, 9 or 10. The more testing cycles are run, the lower is the probability of the controller 22 erroneously releasing the material 9 for conveyance, i.e. of erroneously switching from the ventilating mode to the conveying mode.

A mixed form of the two procedures described above is feasible just as well. Accordingly, the controller 22 can be provided and is operable as follows. At least seven testing cycles are run, whereby the switch from ventilating mode to conveying mode is made only if the tested material of the last three testing cycles, in time, each was classified to be free of bubbles. Otherwise, the controller 22 effects one or more additional testing cycles to be conducted.

The amount of material to be tested by the controller 22 in the ventilating mode can depend on the type of the material 9 and on the requirements considering an error-free decision whether or not and when the switch from ventilating mode to the conveying mode is to be done. If the controller is to test, for example, between 2 and 4 L of material, approximately 40 to 80 testing cycles are run. The machine operator can set the number of testing cycles. The machine operator can also determine, for example, that the controller 22 is to switch from ventilating mode to conveying mode, if no air bubbles are detected any longer in the measuring samples 19, for example after ten testing cycles.

FIGS. 8a to 8d show four different operating states of another possible embodiment of the conveying device 2 based on four block diagrams. The second embodiment of the conveying device 2 differs from the embodiments of the conveying device described above in that the measuring chamber 31 is not accommodated in a separate measuring chamber housing 41, but rather is part of the pump 6. Here, the pump chamber 85 simultaneously serves as measuring chamber by means of which the compressibility of the material to be conveyed and/or of the measuring sample 19 is determined.

The piston pump according to FIG. 8 has a double effect meaning that the piston pump conveys at the pump outlet both during the upward stroke and the downward stroke.

Figure 8A:
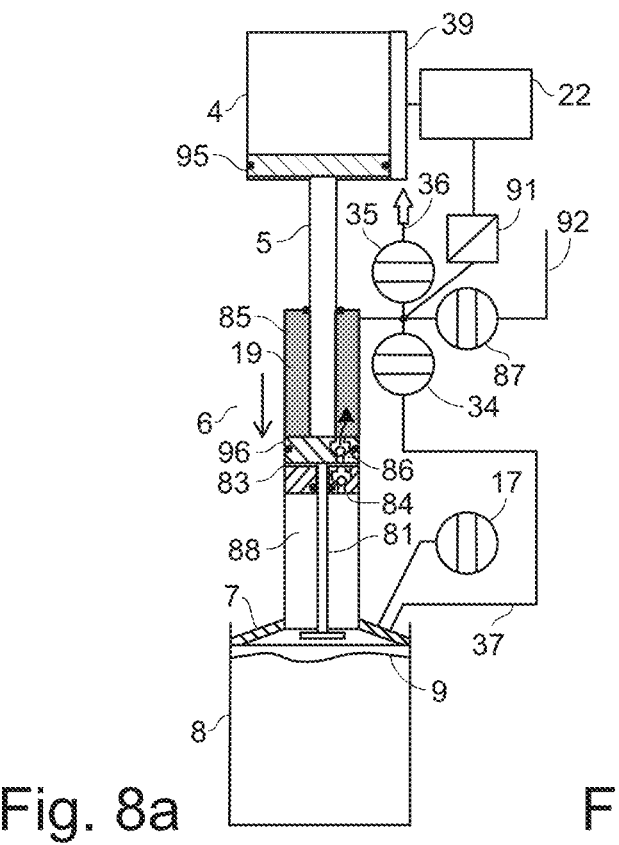
Figure 8B:
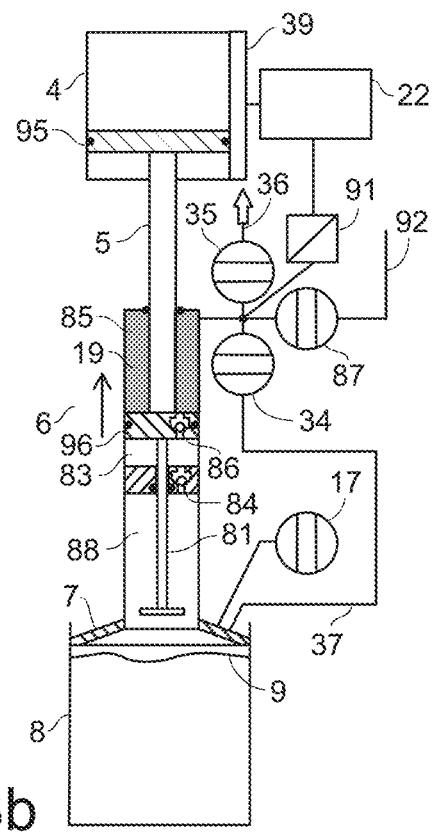
Figure 8C:
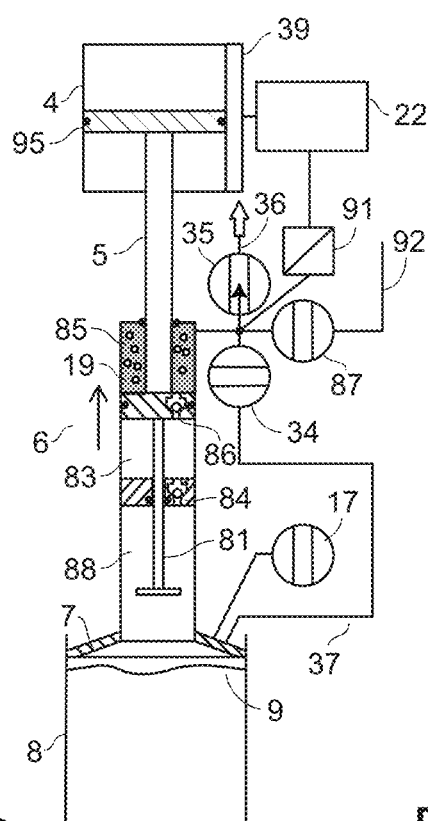
Figure 8D:
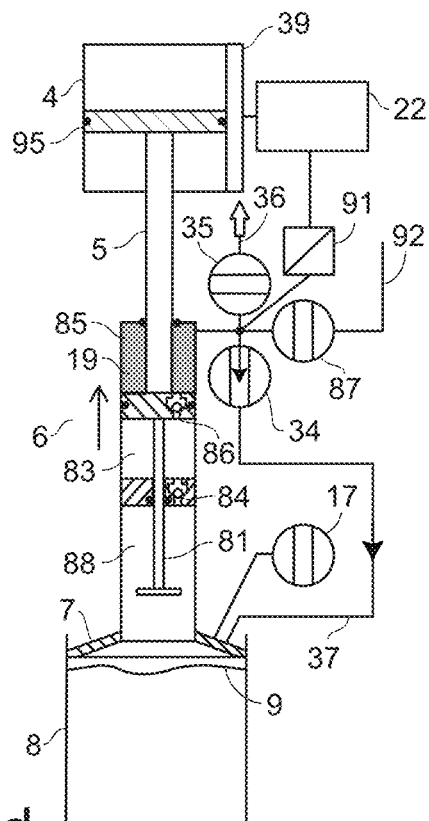
Figure 9A:
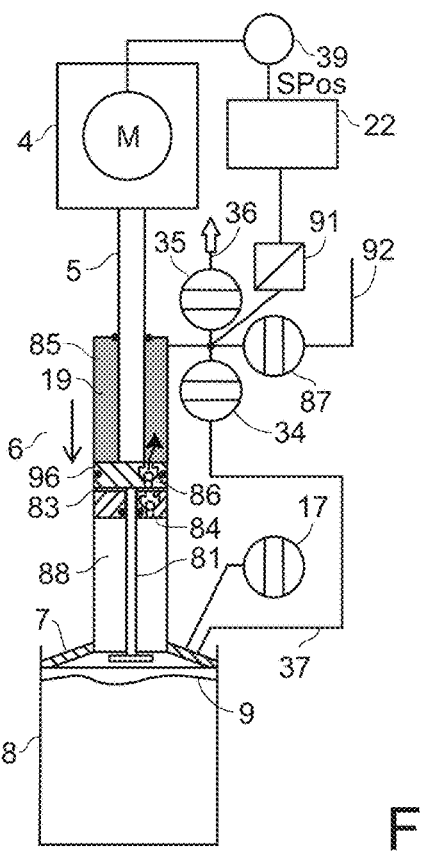
Figure 9B:
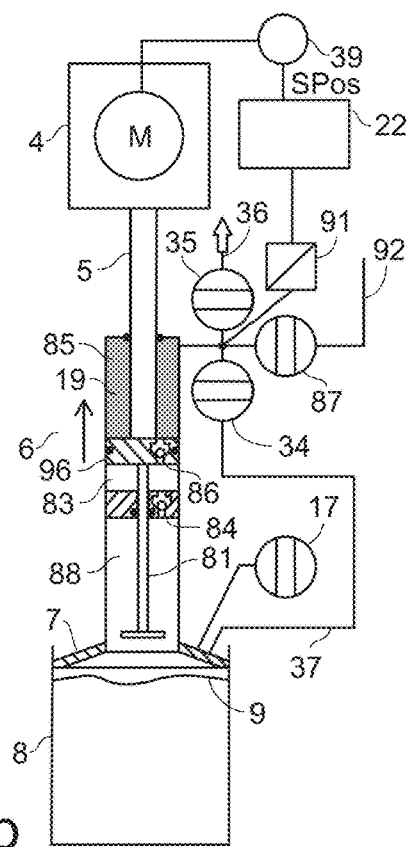
Figure 9C:
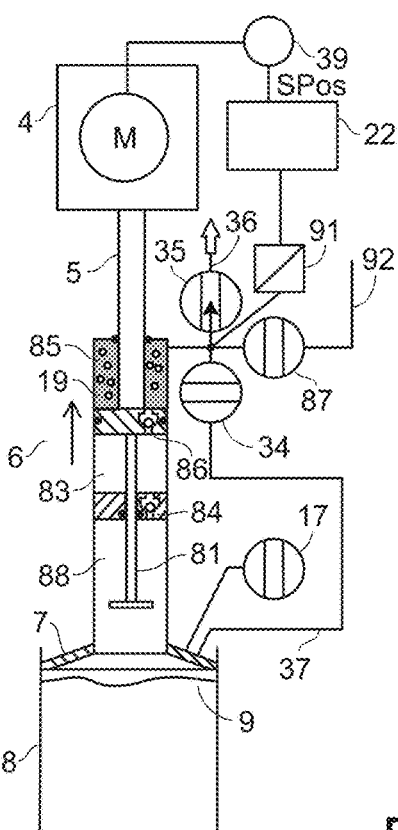
Figure 9D:
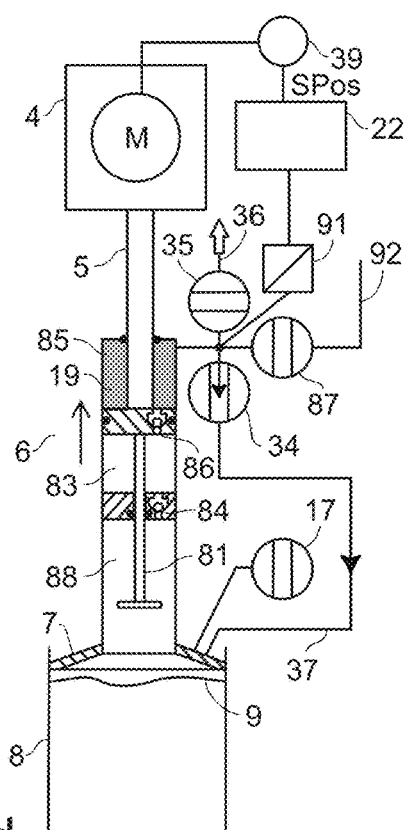

During the downward stroke, the measuring chamber for determining the compressibility of the measuring sample 19 is provided by the lower chamber 83 and the upper chamber 85 (FIG. 8a). During the upward stroke, the measuring chamber is provided by the upper chamber 85 (FIG. 8b).

The embodiment of the conveying device 2 described in FIGS. 8a to 8d works basically in the same way and manner as the embodiment described in FIGS. 7a to 7d. Likewise, the conveying device 2 can be operated in conveying mode or in ventilating mode. In conveying mode, the conveying device 2 uses the pump 6 to convey the viscous material from the container 8.

As has already been described above, the ventilating mode can comprise a first and a second ventilating phase. In order to avoid repetitions, reference shall be made to the description above for illustration of the first ventilating phase.

In the second ventilating phase, the remaining air is removed from the container 8.

For this purpose, the controller 22 can be provided to close the return valve 34, the discharge valve 35, and the conveying valve 87 at the start of the second ventilating phase. Subsequently, the piston 96 is moved upwards with the aid of the drive rod 5 such that a defined pressure is applied in the pump chamber/measuring chamber 85. The position sensor 39 is used to measure the path travelled by the piston 95 during this process. The pump chamber simultaneously serves as measuring chamber 85, and the measured path is a measure of the volume change in the measuring chamber 85. If the result of the measurement is that there still is useful material present in the measuring chamber 85 (usually, this will be material from the previous batch), the controller 22 causes the return valve 34 to be opened. If this is not the case, it causes the discharge valve 35 to be opened and the return valve 34 to stay closed. Then the piston 96 is moved all the way up by means of the drive rod 5 such that the material that is present in the measuring chamber 85 is transported out of the measuring chamber via the valve 34 or 35 that was opened by the controller 22. Simultaneously, the scoop piston 81 is moved upwards along with the upwards motion of the drive rod 5. In this context, the scoop piston 81 conveys material 9 out of the container 8 and through the chamber 88 via the return valve 84 into the lower pump chamber 83.

Once the piston 96 has reached its top end position and, thus, the material has been conveyed out of the pump chamber 85, the previously opened valve 34 or 35 is closed again. Now, another compression measurement can take place. For this purpose, the drive rod 5 and the piston 96 are pushed downwards. Since all outlet-side valves 34, 35, and 87 on the outlet of the pump 6 are closed, the downward motion of the drive rod 5 reduces the total volume (volume of chamber 83 plus the volume of chamber 85) and compresses the measuring sample 19. The compressibility of the measuring sample 19 can now be determined in the way and manner already described above. Once the compression measurement is completed, the return valve 34 or the discharge valve 35 can be opened as a function of the result of the compression measurement and the classification of the material (as described above). The subsequent downward stroke of the piston 96 empties the lower chamber 83. One portion of the material is conveyed out of the lower pump chamber 83 via the return valve 86 into the upper pump chamber 85 and from there out of the pump 6. The other portion of the material is also conveyed out of the lower chamber 83, but remains in the upper chamber 85.

Subsequently, the valve 34 or 35 opened earlier is closed again. FIG. 8a shows the operating state of the conveying device, in which the piston 96 is situated in its lower end position and the valve 34 or 35 is closed again.

After the piston 96 has reached its lower end position, the drive rod 5 with the piston 96 is pulled upwards again in a next step, in which the non-return valve 86 is closed (FIG. 8b). In the process, a defined pressure p is applied to the measuring sample 19 in the upper pump chamber/measuring chamber 85 now.

The path x travelled by the drive rod 5 is measured with the position sensor 39 in a further step. The position sensor 39 can detect, for example, the stroke of the piston 95 that is connected to the drive rod 5. The travelled path x is a measure of the volume change and/or compressibility of the measuring sample 19 that is present in the pump chamber/measuring chamber 85. If there is air in the pump chamber/measuring chamber 85, and therefore in the material, the drive rod 5 travels farther than when the material is free of bubbles. The controller 22 now compares the measured travelled path x of the drive rod 5 to a reference value xref. The analysis of the measuring results and the classification of the measuring samples 19 takes place analogous to the description provided above.

If the air motor 4 is operated at a defined air pressure, the friction arising in the air motor 4 can lead to an error in the determination of the compressibility. In order to compensate for this effect and to be able to determine the compressibility of the measuring sample 19 even more accurately, the conveying device can, in addition, as is shown in FIG. 8, also comprise a pressure sensor 91. The pressure sensor 91 can be used to measure the effective pressure in the measuring chamber 85.

FIGS. 9a to 9d show four different operating states of another possible embodiment of the conveying device 2 based on four block diagrams. The further embodiment of the conveying device 2 differs from the embodiment according to FIG. 8 described above in that the pump drive 4 is not provided as an air motor, but as an electric motor and preferably as a servo motor.

The servo motor 4 uses an integrated incremental encoder to deliver a position signal by means of which the rotational position of the drive shaft of the servo motor, the position of the rod 5 and/or the position of the piston 96 can be determined. The position signal is trans-mitted to the controller 22.

The embodiment of the conveying device 2 described in FIGS. 9a to 9d works basically in the same way and manner as the embodiment described in FIGS. 8a to 8d. Likewise, the conveying device 2 can be operated in conveying mode or in ventilating mode. In conveying mode, the conveying device 2 uses the pump 6 to convey the viscous material from the container 8.

As has already been described above, the ventilating mode can comprise a first and a second ventilating phase. In order to avoid repetitions, reference shall be made to the description provided above with regard to the illustration of the ventilating phases and in particular with regard to the embodiment according to FIG. 8. Rather than detecting the travelled path x of the drive rod 5, the rotational position of the drive shaft of the servo motor can also be detected in the embodiment according to FIG. 9.

The calibration can take place in that the servo motor drives into one end position once, while the chambers 83 and 85 are empty, and the controller 22 then saves the position signal it receives. Subsequently, the servo motor drives into the other end position and the controller 22 then saves the position signal it now receives.

FIGS. 10a to 10c show three different operating states of another possible embodiment of the conveying device 2 based on three block diagrams. The further embodiment of the conveying device 2 differs from the embodiment according to FIG. 9 described above in that the pump 6 is not provided as a scoop piston pump, but as an eccentric screw pump, screw spindle pump, spindle pump or gear type pump. The pump 6 can be operated appropriately such that it permanently attempts to convey material 9 into the chamber 85. For this purpose, the pump 6 can be permanently driven by an electric motor, for example by a servo motor. By this means, a defined volume is set in the chamber 85 and a pressure p is established that is being detected by a pressure sensor 91. The pump 6 comprises a pump actuator 90 that sets the material volume in the measuring chamber 85 and thus establishes the pressure p in the measuring chamber 85. The pump actuator 90 can be the eccentric screw in the case of an eccentric screw pump, the screw spindle in the case of a screw spindle pump, the spindle in the case of a spindle pump, and those cogs in the case of a gear type pump, which es-tablish the pressure p in the measuring chamber 85 and/or set the material volume in the measuring chamber 85.

Comparing a bubble free measuring sample 19 to an air-containing measuring sample, a lower pressure p is established at a defined angle change of the drive shaft of the servo motor 4 in the chamber 85 in the air-containing measures sample 19 than in the bubble-free measuring sample Accordingly, the controller can use the rotational angle signal SPos reflecting the rotational angle of the drive shaft of the servo motor 4, and the pressure P in the chamber 85 to deduce the compressibility of the measuring sample 19. The rotational angle of the drive shaft of the servo motor 4 can be detected using the position sensor 39. If any air is present in the measuring sample 19, a predetermined reference pressure Pref, which is equivalent to a threshold value, is not reached. In contrast, if no air is present in the measuring sample 19, the reference pressure Pref is reached or exceeded. This allows the controller 22 to run the ventilation according to the procedures described above (see, for example, the section on the embodiment according to FIG. 8).

As has already been described above, the ventilating mode can comprise a first and a second ventilating phase. In order to avoid repetitions, reference to the description provided above and, in particular, to the description of the embodiment according to FIGS. 7 and 8 shall be made with regard to the illustration of the ventilating phases.

If the controller 22 determining the compressibility of the measuring sample 19 detects that air-containing material is present in the measuring chamber 85 (FIG. 10b), it opens the discharge valve 35 to dispose the material like in the other embodiments described above, In contrast, if the controller 22 determining the compressibility of the measuring sample 19 detects that useful material is present in the measuring chamber 85 (FIG. 10c), it opens the return valve 34 to return the material into the container 8 like in the other embodiments described above.

The conveying device 2 and/or 102 can be used to convey various viscous materials, for example low-viscosity silicone.

If the conveying system 1 is equipped with two conveying devices 2 and 102, it is also feasible to feed two-component materials, such as two-component silicone under pressure to a downstream mixing unit 200. The materials conveyed separately to the mixer 200 can be mixed in the mixer 200, for example at a ratio of 1:1. If needed, additives can be admixed to the conveyed materials in the mixer 200. This allows to influence the colour or the properties of the material.

Preferably, the follower plate 7 of the conveying device 2 comprises a passage 73 for the return line 37.

Moreover, it is advantageous to provide the valves 33, 34, 35 of the conveying device 2 in the form of needle valves. But this does not have to be the case. One or more of the valves 33, 34, 35 can just as well be provided as ball valves.

Advantageously, the volume of the measuring chamber 31 is less than 50 ccm. But the measuring chamber 31 can just as well comprise a volume of 60 ccm. A smaller measuring chamber volume is advantageous because it allows smaller measuring samples to be drawn. This allows the fraction of losses, i.e. the material classified not to be free of bubbles, to be reduced even further.

The preceding description of the exemplary embodiments according to the present invention is for illustrative purposes only and shall not limit the invention in any way or manner. Various changes and modifications are feasible within the scope of the invention. Accordingly, for example, the different components of the conveying device shown in FIGS. 1 to 8 and/or the conveying devices 2 and 102, can just as well be combined with each other in a way different from the one shown in the Figures.

Moreover, the conveying device 2 according to the invention can be provided to have a quick release device by means of which the measuring device 30 can be connected to and taken off the conveying device 2 and/or 102. This is advantageous, in particular, when multiple conveying devices are present. A single measuring device 30, which can be connected rapidly and easily to the corresponding conveying device, is sufficient for conducting the measurement and, if applicable, the subsequent ventilation. The quick release device is preferably provided appropriately such that the measuring device 30 can be connected to it without any need for tools.

LIST OF REFERENCE NUMBERS

1 Conveying system
2 Conveying device for component A
4 Pump drive
5 Drive rod
6 Pump
7 Follower plate
8 Container
9 Material to be conveyed
10 Yoke
11 Lifting cylinder
13 Guidance
14 Lifting rod
15 Guidance
16 Lifting rod
17 Ventilating valve
18 Motor mount
19 Measuring sample
20 Housing
21 Transport castors
22 Controller
23 Rod
30 Measuring device
31 Measuring chamber
31.1 Measuring chamber inlet
32 Cylinder
33 Inlet valve
34 Outlet or return valve
35 Discharge valve (to the disposal line)
36 Disposal line
37 Material return line
38 Material feed line
39 Position sensor
40 Piston
41 Measuring chamber housing
42 Piston seal
43 T-piece
45.1 Control port
45.2 Control port
46.1 Control port
46.2 Control port
47.1 Control port
47.2 Control port
48 Control port
50 Pressure transducer
51 Outlet component A
52 Drag chain
71 Seal
72 Opening
73 Passage
74 Pressure-active surface
81 Scoop piston
82 Scoop piston plate
83 Pump chamber
84 Non-return valve
85 Pump chamber/measuring chamber
85.1 Pump chamber inlet and/or measuring chamber inlet
86 Non-return valve
87 Conveying valve
88 Chamber
90 Pump actuator
91 Pressure sensor
92 Material transport line
95 Piston
96 Piston
97 Splint
102 Conveying device for component B
104 Pump drive
107 Follower plate
110 Yoke
111 Lifting cylinder
113 Guidance
115 Guidance
118 Motor mount
121 Transport castors
150 Pressure transducer
151 Outlet component B
152 Drag chain
200 Mixing unit
DL Compressed air
SPos Rotational angle signal

The invention claimed is:

1. A conveying device for conveying a viscous material from a container, the conveying device comprising:
a follower plate that can be inserted into the container, and a pump by means of which the viscous material can be conveyed through the follower plate,
a measuring chamber for accommodation of a measuring sample of the viscous material, wherein the measuring chamber has a closeable material inlet opening
a closable disposal line that leads away from the measuring chamber,
a closable material return line that leads from the measuring chamber via the follower plate into the container,
a controller that is designed and can be operated appropriately such that
the controller determines the compressibility of each of a plurality of measuring samples, and
the controller opens the disposal line or the material return line to the measuring sample present in the measuring chamber as a function of the compressibility thus determined.

2. The conveying device according to claim 1, the conveying device further comprising:
an actuator by means of which a predetermined pressure can be generated in the measuring chamber, and
a position sensor for determination of a change of the volume of the measuring chamber.

3. The conveying device according to claim 2,
in which the actuator is a piston or a membrane.

4. The conveying device according to claim 2,
in which the position sensor is provided for detection of the position of the actuator.

5. The conveying device according to claim 2,
in which the controller uses a signal of the position sensor to determine the compressibility of the measuring sample that is present in the measuring chamber.

6. The conveying device according to claim 2,
in which the position sensor is provided as a magnetostrictive sensor.

7. The conveying device according to claim 1, the conveying device comprising:
a pressure sensor for determination of the pressure in the measuring chamber,
wherein the pump comprises a pump actuator by means of which a predetermined volume can be set in the measuring chamber.

8. The conveying device according to claim 1,
in which the measuring chamber is part of the pump.

9. The conveying device according to claim 1,
in which the pump is a piston pump, gear type pump, spindle pump or eccentric screw pump.

10. The conveying device according to claim 1,
in which the follower plate comprises a ventilating valve.

11. The conveying device according to claim 1,
in which the follower plate is slanted in design.

12. The conveying device according to claim 1,
in which the material return line comprises a return valve.

13. A conveying system with a first conveying device and a second conveying device each according to claim 1,
in which the first conveying device and the second conveying device are connected, on the outlet side, to a mixing unit.

14. A method for operating a conveying device according to claim 1, comprising the following steps:
conveying material into the measuring chamber,
after the material inlet opening, the disposal line, and the material return line are closed, the compressibility of the material that is present in the measuring chamber is determined,
the controller is used in accordance with the compressibility thus determined to cause the material that is present in the measuring chamber to be disposed via the disposal line or to be returned into the container via the material return line.

* * * * *